United States Patent
Kreikebaum

[11] Patent Number: 6,091,494
[45] Date of Patent: Jul. 18, 2000

[54] PARTICLE SENSOR WITH COOLED LIGHT TRAP AND RELATED METHOD

[75] Inventor: Gerhard Kreikebaum, San Bernardino, Calif.

[73] Assignee: Venturedyne, Ltd., Milwaukee, Wis.

[21] Appl. No.: 09/318,485

[22] Filed: May 25, 1999

[51] Int. Cl.[7] .......................... G01N 15/02; G01N 21/00
[52] U.S. Cl. ............................................ 356/336; 356/338
[58] Field of Search .................................. 356/336–339, 356/340–343; 362/294, 373; 385/146, 901

[56] References Cited

U.S. PATENT DOCUMENTS

| | | | |
|---|---|---|---|
| 4,176,655 | 12/1979 | Levy | 126/400 |
| 4,298,802 | 11/1981 | Quella et al. | 136/247 |
| 4,434,562 | 3/1984 | Bubley et al. | 101/424.1 |
| 4,582,406 | 4/1986 | Wally | 353/55 |
| 4,974,132 | 11/1990 | Naum | 362/294 |
| 5,032,005 | 7/1991 | Woodruff | 250/498.1 |
| 5,084,621 | 1/1992 | Geiser | 250/352 |
| 5,089,941 | 2/1992 | Howarth | 356/243.1 |
| 5,157,252 | 10/1992 | Gross et al. | 356/225 |
| 5,467,189 | 11/1995 | Kreikebaum et al. | 250/574 |
| 5,731,875 | 3/1998 | Chandler et al. | 356/338 |

*Primary Examiner*—Frank G. Font
*Assistant Examiner*—Layla G. Lauchman
*Attorney, Agent, or Firm*—Jansson, Shupe, Bridge & Munger, Ltd.

[57] ABSTRACT

A particle sensor operates in ambient air at an ambient air temperature and includes (a) a light source projecting a beam of light, (b) a light trap aligned with the beam of light and comprising at least one light-energy-absorbing surface at a surface temperature, (c) a nozzle flowing particle-entraining air through the beam of light, and (d) an opto-electrical system detecting light scattered by a particle. In the improvement, the sensor includes a cooling apparatus in heat transfer relationship to the surface and absorbing heat from such surface. The surface temperature is maintained at or below a value which substantially eliminates thermally-induced electro-optical disturbances in the sensor. A new method for reducing electrical noise detected by an opto-electrical system in the particle sensor includes providing a cooling apparatus in heat transfer relationship to the surface and transferring heat from the surface to the cooling apparatus at a rate which limits the surface temperature to a value which substantially eliminates thermally-induced electro-optical disturbances in the sensor.

17 Claims, 6 Drawing Sheets

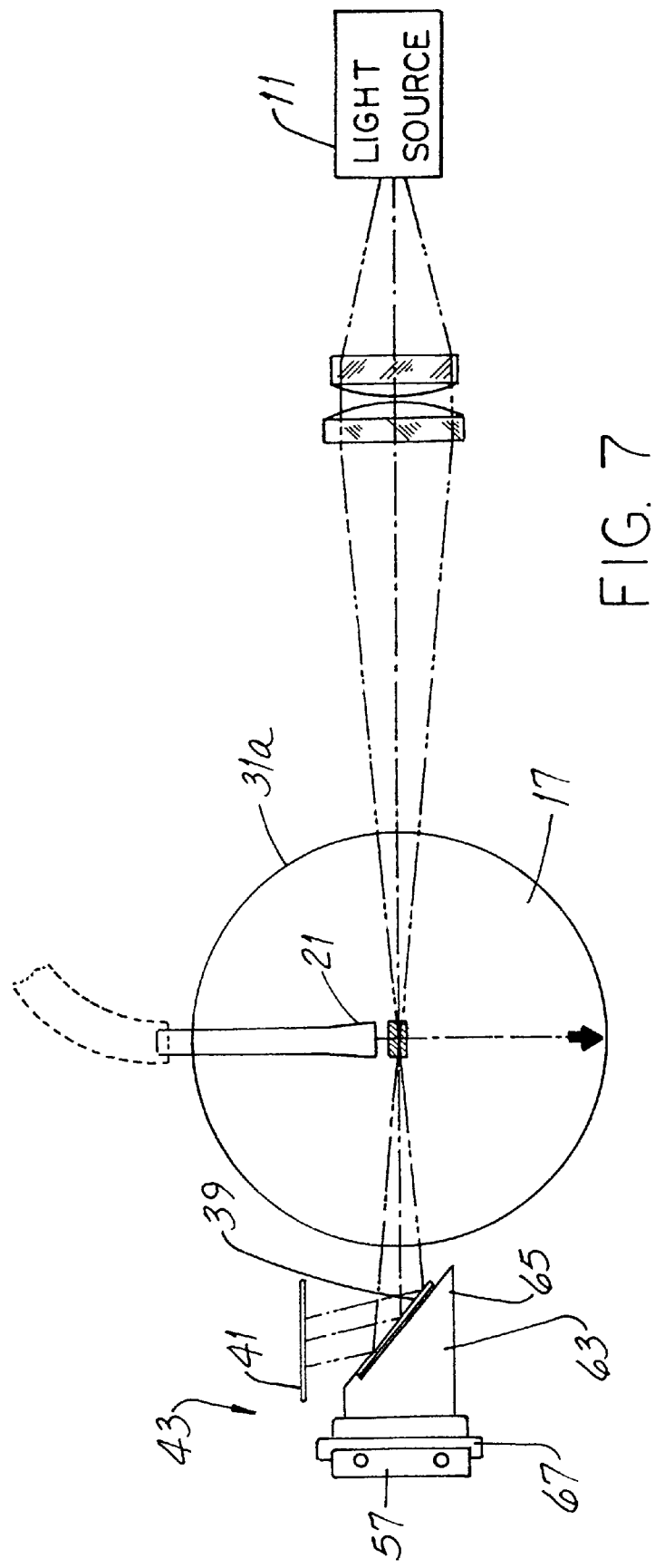

PARTICLE SENSOR WITH COOLED LIGHT TRAP AND RELATED METHOD

FIELD OF THE INVENTION

This invention relates to air quality and, more particularly, to instruments, i.e., particle sensors, for assaying airborne particulates.

BACKGROUND OF THE INVENTION

Particle counters (often called particle sensors) are used to detect light scattered by particles entrained in a stream of fluid, e.g., in an air stream. Such counters draw air (with particles entrained therein) from a room, for example, and flow such air along a tube and through an illuminated sensor "view volume" to obtain information about the number and size of such particles. Such information results from an analysis of the very small amounts of light reflectively "scattered" by the particle as it moves through the view volume.

Such counters direct the air and accompanying particles through the view volume at a particular flow rate (often measured in cubic feet per minute) from one tube (inlet tube) across an open space (view volume) to another tube (outlet tube). In counters of this type, there is no tube wall (however transparent such wall might otherwise be) to impair light scattering and collecting. In other words, the particle is briefly illuminated by a very-small-diameter light beam as it "flies" through an open space.

Among other uses, particle sensors are used to obtain a measure of air quality by providing information as to the number and size of particles present in some specified volume of air, e.g., a cubic meter. Even work environments which appear to human observation to be clean—business offices, manufacturing facilities and the like—are likely to have substantial numbers of microscopic airborne particles. While such particles are not usually troublesome to the human occupants, they can create substantial problems in certain types of manufacturing operations.

For example, semiconductors and integrated chips are made in what are known as "clean rooms," the air in which is very well filtered. In fact, clean rooms are usually very slightly pressurized using extremely clean air so that particle-bearing air from the surrounding environs does not seep in.

And the trend in the semiconductor and integrated chip manufacturing industry is toward progressively smaller geometries. In turn, this requires that particle sensors be able to detect and assay smaller particles than theretofore might have been possible. Since particle characteristics are determined by the amount of light scattered thereby, an apparent solution to the problem of assaying smaller particles involves increasing the intensity of the light beam to increase the quantum of light reflected and scattered by very small and/or fast-moving particles.

In particle counters and sensors using a projected light beam as the light source, it is important to substantially fully attenuate or "kill" the light energy which is not scattered or reflected by a particle passing through the view volume. This is so since stray, "unkilled" light which finds its way to the opto-electrical system or back to the light source itself will degrade sensor performance.

One way to effect light beam attenuation (or "killing") is by using a light trap of the type disclosed in U.S. Pat. Nos. 5,467,189 (Kreikebaum et al.) and 5,731,875 (Chandler et al.). Such patents are incorporated herein by reference.

Such a light trap includes a primary surface or filter made of specially colored glass and having a bulk property. Most of the photon energy of the light beam is transformed into thermal energy in this surface. The light trap also usually includes a secondary surface having a highly light absorbing surface. Such secondary surface is positioned so that any residual light reflected from the primary surface (and there is usually very little of such light) impinges on the secondary surface.

The marketplace demands ever-greater performance of the products made by companies which use particle sensors of the type described above. As a consequence, designers and manufacturers of such particle sensors are being held to ever-higher demands for improved performance. For example, a way to detect very small particles, e.g., 0.1 micron and smaller, and/or to detect particles present in a relatively high air flow volume, e.g., 1 cubic foot per minute, through the sensor is to increase the power level of the light source. But since most of the photon energy emitted by the source must be killed (that is, very little is scattered by a particle), the primary filter or surface must dissipate increasing amounts of thermal energy.

A particle sensor and related method which address the matter of thermal energy dissipation would be an important advance in this field of technology.

OBJECTS OF THE INVENTION

It is an object of the invention to provide a particle sensor and related method which address the matter of thermal energy dissipation.

Another object of the invention is to provide a particle sensor and method which permits assaying very small and/or fast-moving particles.

Yet another object of the invention is to provide a particle sensor and method which limit the light trap surface temperature to a value which substantially eliminates, or at least sharply reduces, thermally-induced electro-optical disturbances in the sensor and spurious electrical "noise" resulting from such disturbances. How these and other objects are accomplished will become apparent from the following descriptions and from the drawings.

SUMMARY OF THE INVENTION

The invention involves a particle sensor operating in ambient air at an ambient air temperature. While typical ambient air temperatures are in the range of 65–75° F., there may be other operating environments where the ambient air temperature is higher or lower.

The sensor is of the type which includes (a) a light source projecting a beam of light and (b) a light trap aligned with the beam of light and comprising at least one light-energy-absorbing surface at a surface temperature. The sensor also has (c) a nozzle flowing particle-entraining air through the beam of light, and (d) an opto-electrical system detecting light scattered by a particle.

It has been discovered that a sensor of the foregoing type exhibits progressively diminished performance as the temperature of the light-energy-absorbing surface rises. And with a higher powered light source such as a laser diode array or a laser diode pumped solid state laser, surface temperature rise is exacerbated.

More particularly, the sensor opto-electrical system and, particularly, the detector and the detector-coupled preamplifier of the analysis instrument, were picking up spurious electrical "noise" at levels above those that would be expected from light scattered by gas molecules in the view volume or sensing region. A surface temperature in the range of 4–8° F. above ambient, and higher, resulted in a significantly increased noise level. Herein, this phenomenon is referred to as thermally-induced electro-optical disturbances. Such disturbances seem to create or in some way be responsible for the spurious electrical noise mentioned above. While the precise nature of this phenomenon is not yet fully understood, it is clear that it occurs.

In the improvement, the sensor includes a cooling apparatus in heat transfer relationship to the surface and absorbing heat therefrom. The surface temperature is maintained at a value which substantially eliminates thermally-induced electro-optical disturbances in the sensor. In specific, exemplary embodiments, the surface temperature is maintained at a value no greater than about 40° F. above the ambient air temperature. More preferably, the surface temperature is no greater than about 20° F. above the ambient air temperature. Most preferably, the surface temperature is no greater than about 4–8° F. above the ambient air temperature. And the surface temperature is maintained above the dewpoint temperature of the ambient air.

In more specific embodiments, the surface cooling apparatus includes a thermoelectric (TE) cooler having a cold side facing toward the surface and a hot side facing away from the surface. The TE cooler may be the only structure transferring heat away from the surface or, in another embodiment, the cooling apparatus may also include a passive heat sink in heat transfer relationship to the hot side of the thermoelectric cooler. And depending upon the amount of light-source-originated heat absorbed by and to be dissipated from the surface, the cooling apparatus may also have a fan flowing air across the passive heat sink. Another type of cooling apparatus capable of transferring heat away from the surface is a heat exchanger having a serpentine path with fluid, either liquid or gas, flowing therethrough.

In one family of embodiments, the active or passive heat sink is in contact with the light-energy-absorbing surface and supports such surface. Stated another way, the surface is mounted on the heat sink.

In another family of embodiments, the cooling apparatus has a metal or other heat-transferring support block with the surface mounted at one end of the block. A heat sink, active or passive, is spaced from the surface and contacts the other end of the support block, thereby removing heat therefrom. Examples of heat sink arrangements used with the support block include a thermoelectric cooler, a heat exchanger having a fluid flowing therethrough, or a hybrid having a heat radiator and an air-moving mechanism flowing air across the heat radiator. Exemplary heat radiators have heat-radiating fins, prongs, pins or similar structure which permit air to circulate therearound.

Other aspects of the invention involve a method for reducing electrical noise detected by an opto-electrical system in a particle sensor of the type described above and operating in ambient air at an ambient air temperature. The method includes providing a cooling apparatus in heat transfer relationship to the surface and transferring heat from the surface to the cooling apparatus at a rate which limits the surface temperature to a value which substantially eliminates—or at least sharply reduces—thermally-induced electro-optical disturbances in the sensor. And when such disturbances are reduced or eliminated, the spurious electrical noise thought to be caused thereby is also reduced or eliminated.

In more specific aspects of the method, the transferring step includes operating a thermoelectric cooler, operating a fan, operating a heat exchanger having a fluid flowing therethrough, or operating some combination of active and passive heat sinks. Or the transferring step may include radiating heat from a passive heat sink.

As used herein, the term "passive heat sink" means a heat transfer device which requires no energy input to perform the heat-transfer function. Example of a passive heat sink include finned and "pronged" heat-radiating devices. The term "active heat sink" means a heat transfer device which requires energy input to perform the heat-transfer function. Examples of an active heat sink include a fan and a TE cooler.

BRIEF DESCRIPTIONS OF THE DRAWINGS

FIG. 7 is a representative elevation view of an embodiment of the new particle sensor using another embodiment of a cooling apparatus in conduction with a light trap surface support block.

DETAILED DESCRIPTIONS OF PREFERRED EMBODIMENTS

Figure 1:
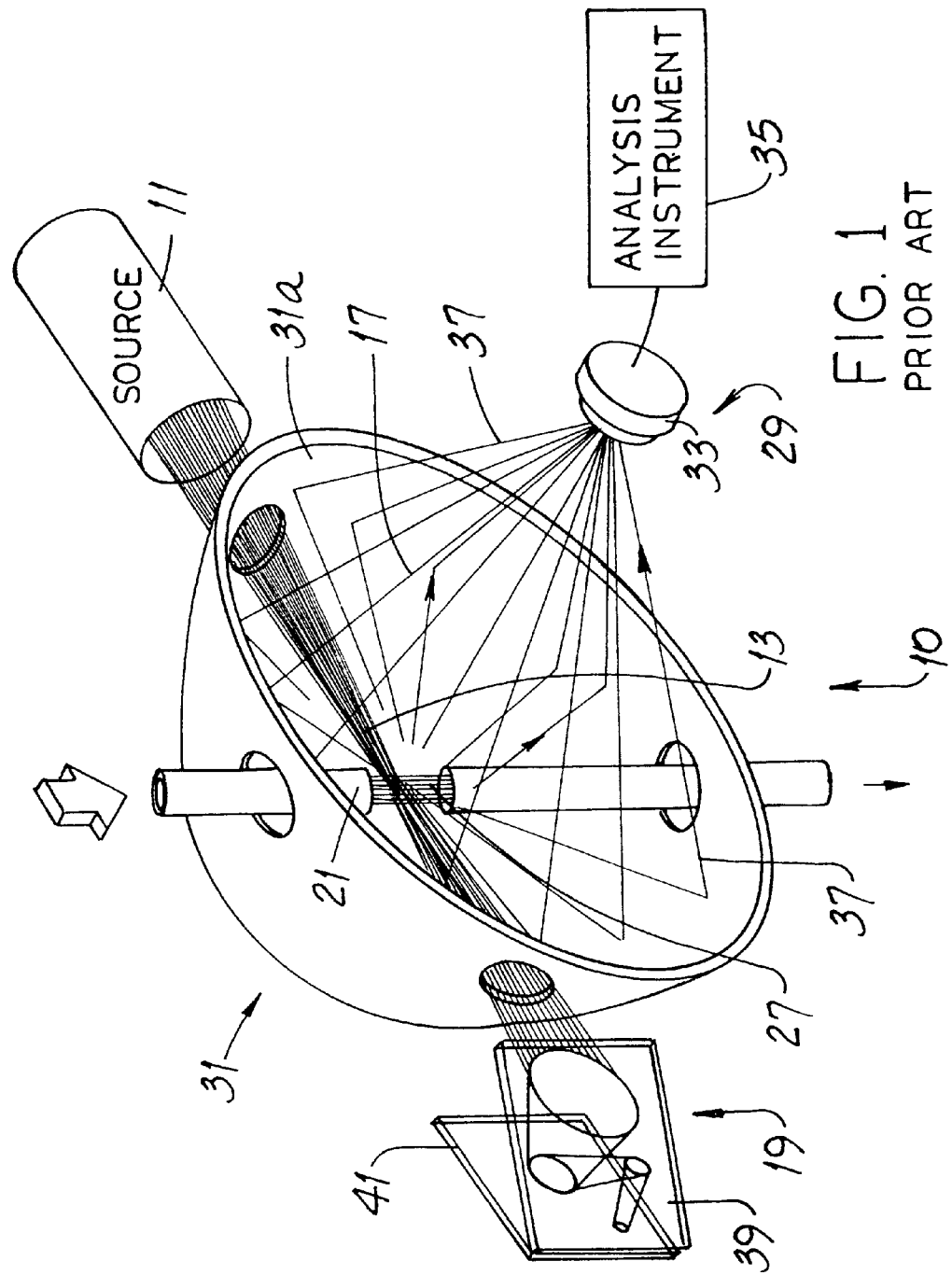
FIG. 1 is a perspective representation of a prior art particle sensor.
Figure 2:
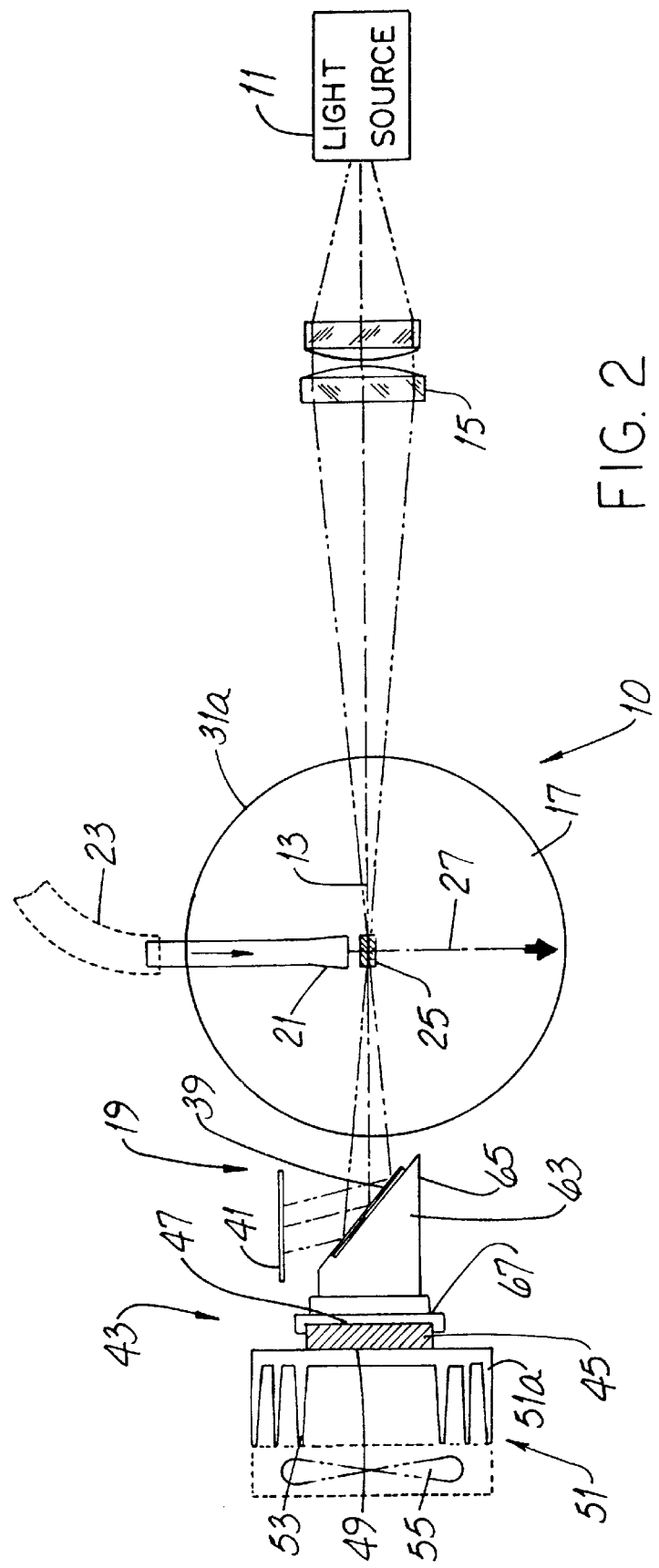
FIG. 2 is a representative elevation view of an embodiment of the new particle sensor using a cooling apparatus in conjunction with a light trap surface support block.

Before describing detailed aspects of the invention, it will be helpful to have an understanding of some of the features of the particle sensor 10 per se. Referring to FIGS. 1 and 2, the sensor 10 includes a light source 11 which may be embodied as a laser diode, a laser diode array or a laser diode pumped solid state laser, to name a few examples.

If the source 11 does not focus light internally and emit a very-small-diameter beam of light 13, such source 11 propagates light to a focusing component 15, e.g., a set of focusing lenses or the like. The focusing lenses focus the light to a linear, very-small-diameter beam of light 13. In either case, the beam of light 13 is projected across a cavity 17 and thence to a light trap 19.

The sensor 10 also has a nozzle 21 which is angular to the beam of light 13 and, preferably, is perpendicular thereto. A vacuum source (not shown) draws air or other gas through the nozzle 21 and exhausts such gas to room ambient. For example, ambient air from the room being monitored for air quality is drawn into the nozzle 21 (perhaps through an optional sampling tube 23), projected through the beam of light 13 and exhausted via the blower. The sensing volume or view volume 25 is a very-small, somewhat-cylinder-shaped volume generally defined by the intersection of the beam of light 13 and the air stream 27.

The sensor 10 also has an opto-electrical system 29 comprising an optical device 31 for gathering reflected light and an electrical apparatus including a detector 33 and an analysis instrument 35 connected to the detector 33. In the exemplary embodiment, the optical device 31 is an ellipsoidal mirror 31a. The aforedescribed components are arranged in such a way that the intersection of the beam of light 13 and the air stream 27 (and, therefore, the sensing volume 25) is at one focal point of the mirror 31a and the detector 33 is at the other focal point. (It is to be appreciated that other types of optical arrangements, e.g., light-gathering lenses, may be used in lieu of an ellipsoidal mirror 31a.)

As small, air-entrained particles leave the nozzle 21 and "fly" through the sensing volume 25, they reflect or "scatter" light. Such scattered light, represented by the light ray lines 37, strike the ellipsoidal mirror 31a and are reflected to the detector 33. The beam of light 13 continues to the light trap 19 aligned therewith where such beam of light 13 is "killed," i.e., substantially fully attenuated.

The photon energy impinging on the detector 33 is converted to electrical signals which are analyzed in the instrument 35. From such analyzed signals, both the size and number of particles flying through the sensing volume 25 (as well as other particle-related information) can be ascertained. And, of course, this information is indicative of the level of cleanliness of ambient air in the room.

Figure 3:
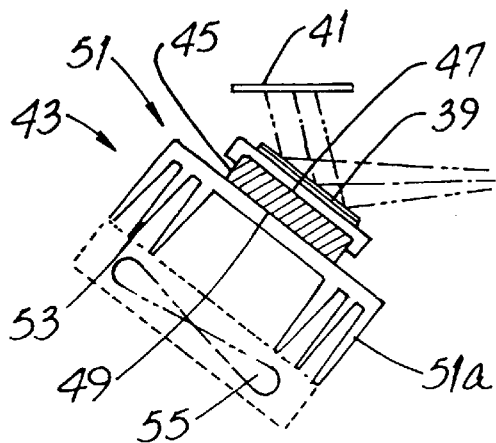
FIGS. 3, 4, 5 and 6 are representative elevation views of aspects of the new particle sensor using different embodiments of a cooling apparatus to directly support the light trap surface.
Figure 4:
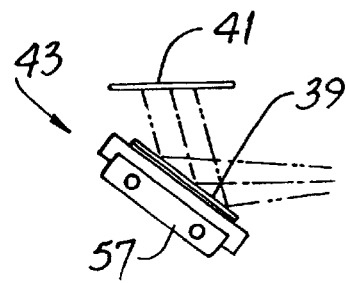
Figure 5:
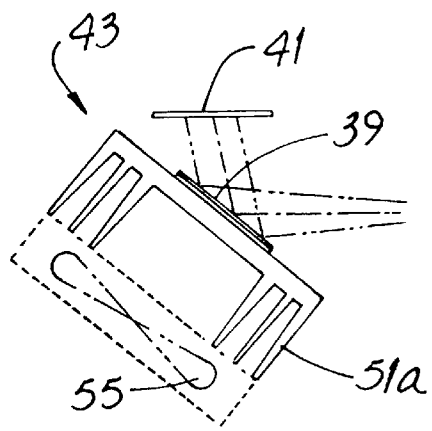

Referring now to FIGS. 1, 2, and 3, the light trap 19 comprises a primary light-energy-absorbing surface 39 and a secondary light-energy-absorbing member 41 made both of filter glass. While the surface 39 and member 41 are shown as being substantially planar, other light trap arrangements are possible and contemplated by the invention.

While a high percentage, e.g., 95%, of the photon energy of the beam of light 13 is absorbed (or killed) by the surface 39, the member 41 receives any unabsorbed light reflected by the surface 39 and substantially fully attenuates it. The photon energy is converted to heat. From the foregoing, it is apparent why the temperature of the surface 39 has a propensity to rise if the light source 11 is a high-energy-output source such as a high power laser, laser diode array or a laser diode pumped solid state laser.

Referring now to FIGS. 2–10, the sensor 10 includes a cooling apparatus 43 in heat transfer relationship to the surface 39 and absorbing heat therefrom. Heat is transferred from the surface 39 to the apparatus 43 at such a rate that the surface temperature is thereby maintained at a value which substantially eliminates or greatly reduces thermally-induced electro-optical disturbances in the sensor 10 and, more specifically, in the sensing cavity 17. In turn, electrical noise detected by the detector 33 and caused by (or thought to be caused by) such disturbances are reduced or substantially eliminated.

In specific embodiments of the sensor 10, the surface temperature is held to a value no greater than about 40° F. above the ambient air temperature, more preferably no greater than about 20° F. above the ambient air temperature and most preferably, no greater than about 4–8° F. above the ambient air temperature. And to avoid "fogging" the surface 39, its temperature is maintained above the dewpoint temperature of the ambient air. (A surface 39 coated with condensed water droplets is of vastly diminished effectiveness in attenuating light.)

Referring particularly to FIGS. 2, 3, 6 and 8, and, the surface cooling apparatus 43 includes a thermoelectric (TE) cooler 45 having a cold side 47 facing toward the surface 39 and a hot side 49 facing away from the surface 39. The TE cooler 45 may be the only structure transferring heat away from the surface 39. Or as represented in FIGS. 2 and 3, the cooling apparatus 43 may also include a passive heat sink 51 in heat transfer relationship to the hot side 49 of the thermoelectric cooler 45.

In an exemplary embodiment, the passive heat sink 51 is a heat radiator 51a made of a material, e.g., aluminum or copper, having very good heat-transfer characteristics. The exemplary radiator 51a shown in FIGS. 2 and 3 has fins 53 or prongs which radiate heat to the surrounding air. And depending upon the amount of light-source-originated heat absorbed by and to be dissipated from the surface 39, the cooling apparatus 43 may also have a fan 55 flowing air across the passive heat sink 51.

Referring particularly to FIGS. 4, 6 and 7–10, another type of cooling apparatus 43 capable of transferring heat away from the surface 39 is a heat exchanger 57 of the type having a serpentine conductor 59 with fluid, either liquid or gas, flowing therethrough. Heat from the surface 39 migrates through the exchanger block 51, is absorbed by the fluid flowing through the conductor 59 and "given up" by such fluid at a location away from the surface 39.

Figure 6:
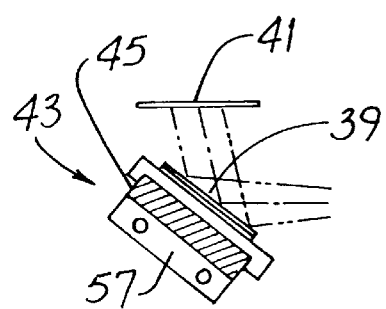
Figure 10:
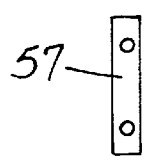
FIG. 10 is an edge elevation view of the cooling apparatus of FIG. 9 taken along the viewing plane 10—10 thereof.
Figure 9:
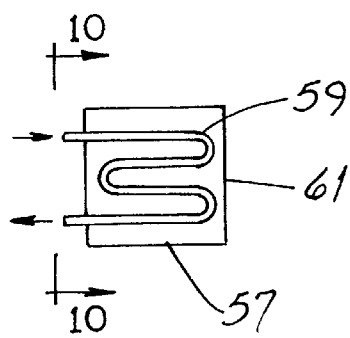
FIG. 9 is a representative elevation view of a cooling apparatus embodied as a serpentine heat exchanger.
Figure 8:
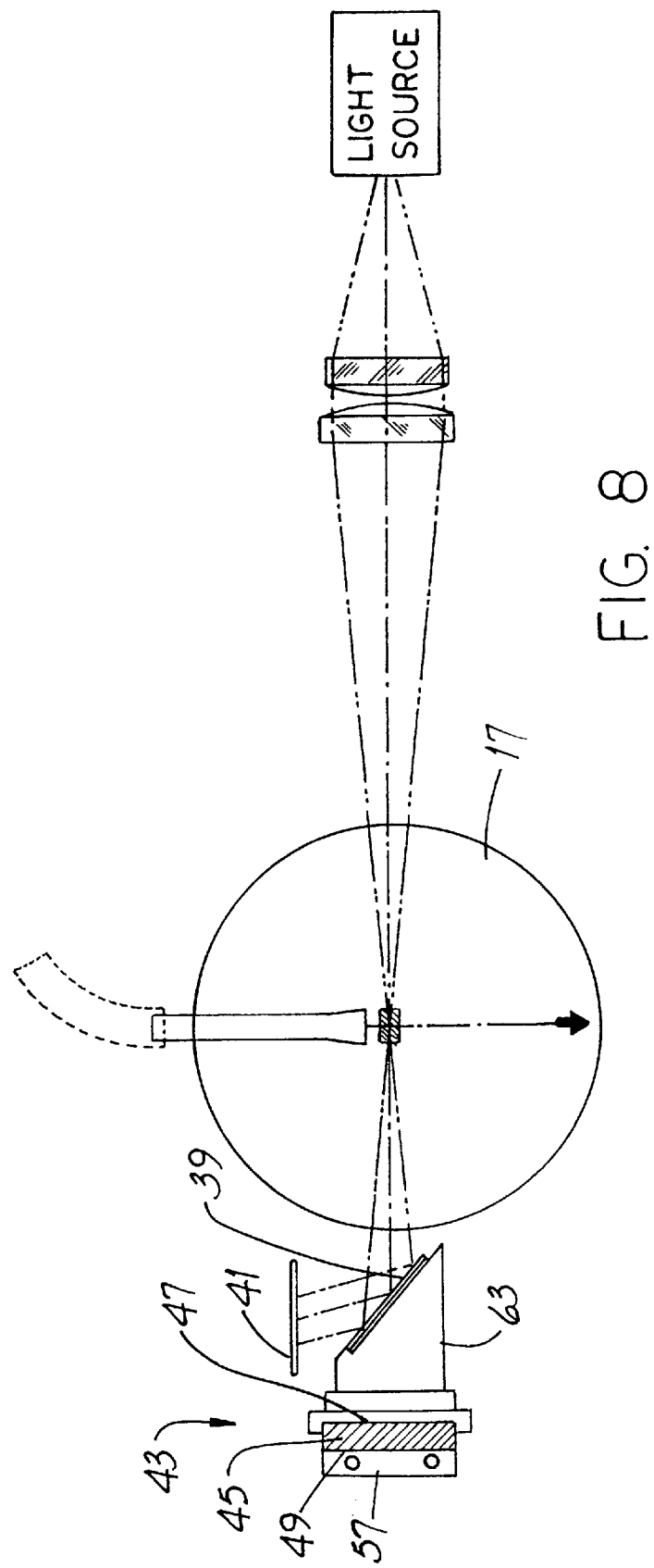
FIG. 8 is a representative elevation view of an embodiment of the new particle sensor using yet another embodiment of a cooling apparatus in conduction with a light trap surface support block.

In one family of embodiments of the sensor 10, the active heat sink or the passive heat sink (as the case may be) is in contact with the light-energy-absorbing surface and supports such surface 30. In the embodiments of FIGS. 3 and 6, the TE cooler 45 directly supports the surface 39. In that of FIG. 4, the heat exchanger 57 supports the surface 39 and in that of FIG. 5, the radiator 51a supports the surface 39.

Figure 11:
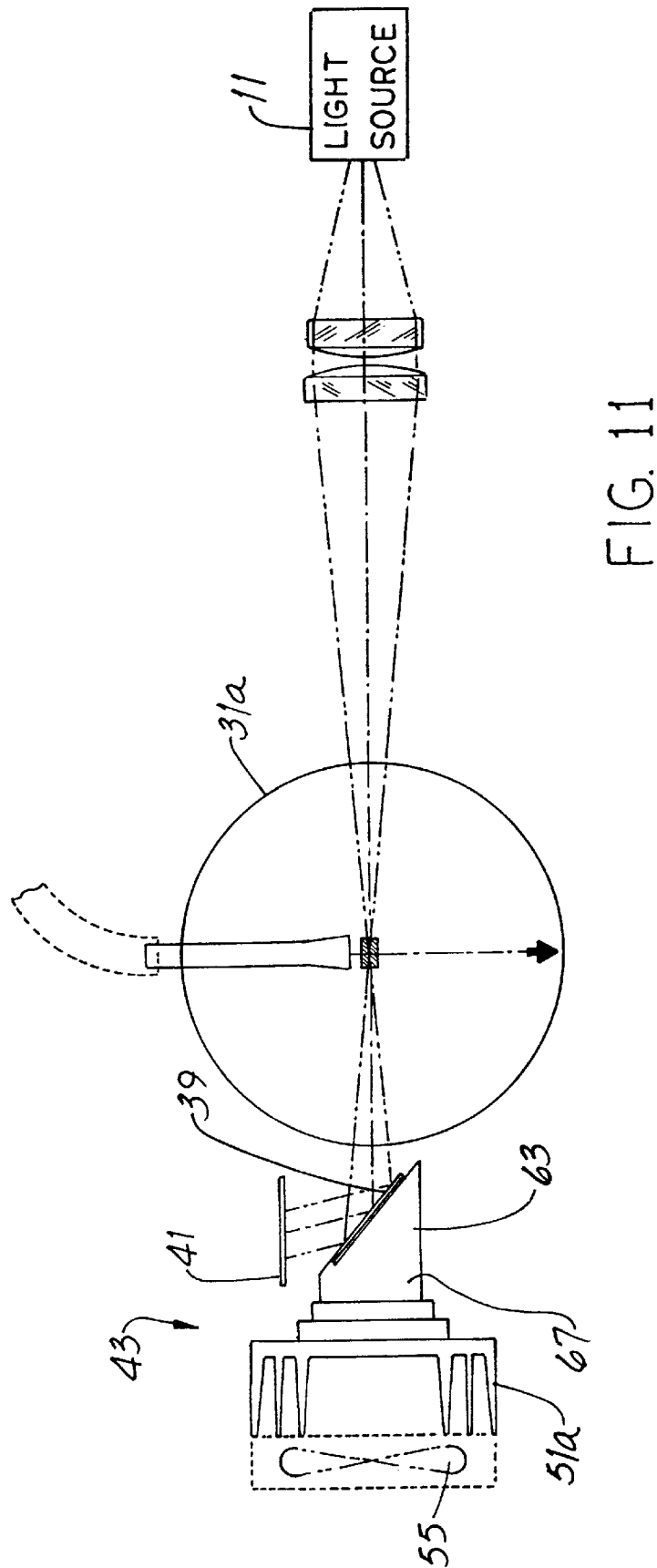
FIG. 11 is a representative elevation view of an embodiment of the new particle sensor using still another embodiment of a cooling apparatus in conduction with a light trap surface support block.

Referring to FIGS. 2, 7, 8 and 11, in another family of embodiments, the cooling apparatus 43 has a metal or other heat-transferring support block 63. An exemplary block 63 is circular in cross-section, is hollow or solid, resembles a truncated cylinder, and has the surface 39 mounted at one end 65. A heat sink, active or passive, is spaced from the surface 39 and contacts the other end 67 of the support block 63, thereby removing heat therefrom. Examples of heat sink arrangements used with the support block 63 include a thermoelectric cooler 45 (FIGS. 2, 8), a heat exchanger 57 having a fluid flowing therethrough (FIG. 7), or a hybrid having a heat radiator 51a and an air-moving mechanism, e.g., a fan 55, flowing air across the heat radiator 51a (FIGS. 2, 11). (The invention contemplates the possibility of combinations of differing types of heat sinks. For example, the version of FIG. 8 includes both a TE cooler 45 in heat transfer relationship to the block 63 and a fluid heat exchanger 57 in heat transfer relationship to the cooler 45.)

Referring to the FIGS. 1–11, other aspects of the invention involve a method for reducing electrical noise detected by an opto-electrical system in a particle sensor 10 of the type described above and operating in ambient air at an ambient air temperature. The method includes providing a cooling apparatus 43 in heat transfer relationship to the surface 39 and transferring heat from the surface 39 to the cooling apparatus 43 at a rate which limits the surface temperature to a value which substantially eliminates thermally-induced electro-optical disturbances in the sensor 10. Temperature rise values for specific embodiments are set out above.

The transferring step includes operating a thermoelectric cooler 45, operating a fan 55, operating a heat exchanger 57 having a fluid flowing therethrough, or operating some combination of active and passive heat sinks. Or the transferring step may include radiating heat from a passive heat sink such as the heat radiator 51*a*.

While the principles of the invention have been shown and described in connection with preferred embodiments, it is to be understood clearly that such embodiments are by way of example and are not limiting.

What is claimed:

1. In a particle sensor operating in ambient air at an ambient air temperature and including (a) a light source projecting a beam of light, (b) a light trap aligned with the beam of light and comprising at least one light-energy-absorbing surface at a surface temperature, (c) a nozzle flowing particle-entraining gas through the beam of light, and (d) an opto-electrical system detecting light scattered by a particle, the improvement wherein:

the sensor includes a cooling apparatus in heat transfer relationship to the surface and absorbing heat therefrom; and the surface temperature is thereby maintained at a value which substantially eliminates thermally-induced electro-optical disturbances in the sensor.

2. The sensor of claim 1 wherein:

the ambient air has a dewpoint temperature; and the surface temperature is above the dewpoint temperature.

3. The sensor of claim 1 wherein:

the cooling apparatus includes a thermoelectric cooler having a cold side facing toward the surface and a hot side facing away from the surface.

4. The sensor of claim 3 including a passive heat sink in heat transfer relationship to the hot side of the thermoelectric cooler.

5. The sensor of claim 4 including a fan flowing air across the passive heat sink.

6. The sensor of claim 1 wherein the cooling apparatus includes a heat exchanger having a fluid flowing therethrough.

7. The sensor of claim 6 wherein the cooling apparatus also includes a thermoelectric cooler.

8. The sensor of claim 1 wherein:

the cooling apparatus has a support block with the surface mounted thereon; and a heat sink is spaced from the surface and contacts the support block, thereby removing heat therefrom.

9. The sensor of claim 8 wherein the heat sink is an active heat sink including a thermoelectric cooler.

10. The sensor of claim 8 wherein the heat sink is an active heat sink including a heat exchanger having a fluid flowing therethrough.

11. The sensor of claim 8 wherein the heat sink includes a heat radiator and an air-moving mechanism flowing air across the heat radiator.

12. A method for reducing thermally-induced electrical noise detected by an opto-electrical system in a particle sensor operating in ambient air at an ambient air temperature and including (a) a light source projecting a beam of light, (b) a light trap aligned with the beam of light and comprising at least one light-energy-absorbing surface at a surface temperature, (c) a nozzle flowing particle-entraining air through the beam of light, and (d) the opto-electrical system, the method including:

providing a cooling apparatus in heat transfer relationship to the surface; and transferring heat from the surface to the cooling apparatus at a rate which limits the surface temperature to a value which substantially eliminates thermally-induced electro-optical disturbances in the sensor.

13. The method of claim 12 wherein the transferring step includes transferring heat from the surface to the cooling apparatus at a rate which limits the surface temperature to a value no greater than about 40° F. above the ambient air temperature.

14. The method of claim 12 wherein the transferring step includes operating a thermoelectric cooler.

15. The method of claim 12 wherein the transferring step includes operating a fan.

16. The method of claim 12 wherein the transferring step includes operating a heat exchanger having a fluid flowing therethrough.

17. The method of claim 12 wherein the transferring step includes radiating heat from a passive heat sink.

\* \* \* \* \*

UNITED STATES PATENT AND TRADEMARK OFFICE
CERTIFICATE OF CORRECTION

PATENT NO.   : 6,091,494
DATED        : July 18, 2000
INVENTOR(S)  : Gerhard Kreikebaum It is certified that error appears in the above-identified patent and that said Letters Patent is hereby corrected as shown below:

Column 4,
Line 29, cancel "conduction" and insert -- conjunction --.
Line 42, cancel "conduction" and insert -- conjunction --.

Column 6,
Line 12, cancel "51 a" and insert -- 51a --.

Signed and Sealed this

Seventh Day of June, 2005

JON W. DUDAS
*Director of the United States Patent and Trademark Office*